United States Patent [19]

Vofsi et al.

[11] 3,954,876
[45] May 4, 1976

[54] PRODUCTION OF HALO-SUBSTITUTED DERIVATIVES OF ACETOPHENONE

[75] Inventors: David Vofsi, Rehovot; Jonathan Freddy Cohen, Bat-Yam, both of Israel; Michael Martan, Evanston, Ill.

[73] Assignee: Yeda Research and Development Co., Ltd., Rehovot, Israel

[22] Filed: Nov. 4, 1974

[21] Appl. No.: 520,461

Related U.S. Application Data

[63] Continuation-in-part of Ser. No. 317,590, Dec. 22, 1972, abandoned.

[30] Foreign Application Priority Data

Jan. 24, 1972  Israel............................. 38629

[52] U.S. Cl............................ 260/592; 260/618 C; 252/431 R
[51] Int. Cl.²....................................... C07C 29/00
[58] Field of Search................................. 260/592

[56] References Cited
UNITED STATES PATENTS

| | | | |
|---|---|---|---|
| 2,854,488 | 9/1958 | Widiger | 260/592 X |
| 2,861,984 | 11/1958 | Gordon et al. | 260/592 X |
| 2,954,405 | 9/1960 | Hoch et al. | 260/610 |
| 3,538,165 | 11/1970 | Rutherford | 260/592 |
| 3,666,815 | 5/1972 | Scheltus | 260/592 |

Primary Examiner—James O. Thomas, Jr.
Assistant Examiner—James H. Reamer
Attorney, Agent, or Firm—Hubbell, Cohen, Stiefel & Gross

[57] ABSTRACT

A process for producing halosubstituted derivatives of acetophenone from the respective halocumenes, the term "halo" as used herein, signifying chlorine or bromine, the molecule containing 1 to 3 nuclear halo substituents in the meta- and/or paraposition relative to the isopropyl group. The process comprises oxidizing the halocumene by means of air or oxygen. The oxidation is effected in the presence of a metal phthalocyanine complex as catalyst, and in a most preferred embodiment, in the co-presence of a dichlorobenzene solvent. The preferred halocumenes are p-chlorocumene and p-bromocumene.

8 Claims, No Drawings

PRODUCTION OF HALO-SUBSTITUTED DERIVATIVES OF ACETOPHENONE

CROSS REFERENCE TO RELATED APPLICATIONS

This is a continuation-in-part of co-pending application, Ser. No. 317,590, filed on Dec. 22, 1972 now abandoned.

BACKGROUND OF THE INVENTION

1. Field of the Invention

The invention relates to catalytic oxidation processes, and in particular, to such processes for producing haloacetophenones from the corresponding halocumenes while simultaneously minimizing the co-production of the corresponding halocarbinol which is an undesirable side product.

2. Prior Art

It is known that acetophenone and substituted acetophenones may be obtained by the liquid-phase oxidation of the respective ethylbenzenes. The rate of oxidation in this method, is however, slow, and undesirable by-products are obtained.

The liquid-phase oxidation of cumene (isopropylbenzene) by means of air or oxygen is also well known. When this process is effected in the absence of a catalyst, and at temperatures around 100°C, cumene hydroperoxide is produced. When this process is effected in the presence of catalysts, such as transition metal salts, and, in particular, certain salts of cobalt, a mixture of acetophenone and methylphenyl carbinol in a mole ratio of about 1:1 is obtained. A similar molar ratio of products is obtained by the oxidation of halogen-substituted cumenes. The presence of large amounts of the obtained carbinol as a by-product is undesirable, because the need to either separate the products or convert the carbinol to the acetophenone adversely affects the economy of the process.

In U.S. Pat. No. 2,954,405, there is disclosed a process for the catalytic autooxidation of cumenes to produce the corresponding cumene hydroperoxide. These hydroperoxides, which are intermediates for the preparation of phenols are desirable products and accordingly, the maximizing of the yield of the hydroperoxide is of major significance in this patent. Of course, the simultaneous minimizing of the yield of the corresponding acetophenone is also desired.

In U.S. Pat. No. 2,291,915 there is disclosed a process for the preparation of styrenes by oxidizing a cumene in the absence or presence of a catalyst. This oxidation produces an approximately 1:1 mixture of the corresponding acetophenone and carbinol which is then subjected to further treatment to convert them to the desired styrene. When the cumene is oxidized in highly basic media, the carbinol is the main reaction product.

In none of this prior art is there any suggestion that the oxidation of a cumene can be so effected as to maximize the yield of the acetophenone and simultaneously minimize the yield of the carbinol (and the hydroperoxide).

SUMMARY OF THE INVENTION

An object of the present invention is to provide a novel process for the production of halo-substituted acetophenone derivatives.

In accordance with that object, it has now been found that the oxidation of halocumenes can be conducted in a manner which leads to the preferential production of the corresponding haloacetophenones with a simultaneous reduction in the relative amount of the corresponding halocarbinols, the latter being undesirable side products.

In particular, it has been found that when the air (or oxygen) oxidation of halocumenes is effected at temperatures between 50° and 200°C, preferably, between 130° and 160°C, with the use of a metal phthalocyanine catalyst, and most preferably, in the co-presence of an inert solvent such as a dichlorobenzene, the oxidation product principally comprises the desired haloacetophenone with relatively small amounts of the undesired corresponding halocarbinol. In its most preferred embodiment, the invention provides a process wherein the ratio of the haloacetophenone to the halocarbinol in the oxidation product is 16:1 as compared with the known processes wherein this ratio is generally about 1:1.

In accordance with the process of the present invention, the overall molar yield of the haloacetophenones with respect to the halocumene starting material is well over 90%.

The process according to the invention comprises oxidizing a halo-substituted cumene in the liquid phase by means of air or oxygen at a temperature in the range of between 50° and 200°C, preferably between 130° and 160°C, at a pressure of 0.2–50 atm., preferably 1–10 atm. in the presence of a catalytic amount of a metal phthalocyanine complex, generally, about 0.1% by weight of the halocumene, whereby about 30–90% of the starting halocumene is converted to the corresponding haloacetophenone. The haloacetophenone constitutes the major product of the oxidation reaction, with the corresponding halocarbinol being produced in lesser quantities along with minor amounts of formaldehyde.

The molar ratio of the haloacetophenone to the halocarbinol in the oxidation product is a function of the duration of the reaction. By extending the reaction for prolonged periods, i.e., to about 2–4 hours, this ratio increases as the proportion of halocarbinol approaches zero.

The metal phthalocyanines which may be used in the process include copper, cobalt and iron phthalocyanines.

In its most preferred embodiment, the process of the invention comprises running the above described oxidation in the copresence of an inert solvent such as a dichlorobenzene, preferably, o-dichlorobenzene. Under these conditions, the highest conversion of the starting halocumene is achieved, with the ratio of the produced haloacetophenone to halocarbinol being at its highest. The separation of the unreacted halocumenes and the by-product halocarbinol from the haloacetophenone is effected using conventional separation techniques.

DESCRIPTION OF THE PREFERRED EMBODIMENTS

The invention is illustrated by the following examples of the preferred embodiments thereof, the invention, of course, not being limited thereto.

EXAMPLE 1 (Not within the scope of the invention)

200 gm. of p-chlorocumene were subjected to oxidation in a 500 ml. round bottom flask provided with mechanical stirrers, by means of oxygen at atmospheric pressure, at a temperature of 120°C, and in the presence of 0.2 gm. of chromic-stearate as catalyst.

The reaction was discontinued after 3 hours and the product was analyzed by gas-liquid chromatography. The product was found to contain 62% of unreacted p-chlorocumene, 26% p-chloroacetophenone, and 10% 1-p-chlorophenyl-isopropanol. Thus, the ratio of the desired p-chloroacetophenone to the undesired corresponding carbinol, i.e., 1-chlorophenyl-isopropanol was 2.6:1.

EXAMPLE 2

1 kg. of p-bromocumene was placed in a 316 stainless steel, magnetically stirred reactor of 2 liter capacity. 1 gm. of copper phthalocyanine (Irgalith Blue BL, a CIBA-GEIGY product), was used as the catalyst. The contents of the reactor were heated to 150°C, and a current of air was passed through the reaction mixture such that, in the exiting gas, the concentration of oxygen was kept below 8% by volume. The temperature, during the reaction was maintained in the range of 150°–160°C.

Table 1 summarizes the results obtained in this example as well as the results obtained when this example is repeated using, instead of copper phthalocyanine, other metal phthalocyamine catalysts, such as cobalt and iron phthalocyanine. The cobalt and iron phthalocyanine compounds were prepared in accordance with the procedures described by Moser — Phthalocyanine Compounds, Chap. 3, Reinhold Publishing Corporation, N.Y. 1963.

tained in the range of 140°–150°C. After 4 hours reaction time, a 50% conversion of the p-bromocumene was obtained, producing 48% of p-bromoacetophenone and 3% of 2-p-bromophenyl isopropanol. This example clearly demonstrates that when the oxidation is run in an inert solvent such as a dichlorobenzene, as well as in the presence of a metal phthalocyanine catalyst, the production of the desired haloacetophenone is markedly increased in relation to the production of the co-produced carbinol. Thus, the ratio of the haloacetophenone to carbinol is 16:1 as contrasted with ratios, ranging from 1.5:1 to 10:1 when no solvent is used; see Table 1.

EXAMPLE 4

200 gm. of 3,4-di-chlorocumene were oxidized as described in Example 3. After discontinuing the oxidation, 100 gm. of 3,4-dichloroacetophenone were isolated by fractional distillation. (95% Yield based on the reacted 3,4-dichlorocumene). The product was identified by gas-liquid chromatography using an authentic sample for comparison; M.P. = 74°C.

EXAMPLE 5

200 gm. of 3,4-dibromocumene were oxidized as described in Example 3, yielding 100 gm. of 3,4-dibromoacetophenone, i.e., a yield of 95% based on the converted 3,4-dibromocumene; M.P. = 63°C.

In Example 1, which describes the use of a catalyst outside the scope of the invention, while the ratio of the yield of haloacetophenone to carbinol is 2.6 to 1, the overall yield or conversion is rathter low, with 62% of the starting halocumene being unreacted.

In contrast, in Example 2, which is within the scope of the invention, the ratio of the yield of haloacetophenone to carbinol varies from 1.6 to 1 to 11 to 1. How-

TABLE 1

OXIDATION OF P-BROMOCUMENE IN THE PRESENCE OF METAL PHTHALOCYANINES AS CATALYST; REACTION TEMPERATURE 150°; 0.1% (wt) CATALYST

| Reaction Time in Hours | Conversion % of reacted p-bromocumene | | | mol % p-bromo acetophenone | | | mol% 2-p-bromo phenyl isopropanol | | | % Yield=p-bromo-acetophenone+2-p-bromophenyl isopropanol/ reacted p-bromocumene | | | Ratio of p-bromo-acetophenone to 2-p-bromophenyl isopropanol | | |
|---|---|---|---|---|---|---|---|---|---|---|---|---|---|---|---|
| | METAL PHTHALOCYANINE | | | | | | | | | | | | | | |
| | Copper | Cobalt | Iron | Copper | Cobalt | Iron | Copper | Cobalt | Iron | Copper | Cobalt | Iron | Copper | Cobalt | Iron |
| 2 | 50 | 60 | 57 | 28 | 40 | 38 | 18 | 16 | 15 | 92 | 93 | 93 | 1.6 | 2.5 | 2.5 |
| 3 | 56 | 67 | 62 | 33 | 50 | 45 | 17 | 10 | 11 | 90 | 90 | 89 | 1.9 | 5 | 4.1 |
| 4 | 60 | 69 | 65 | 42 | 55 | 49 | 11 | 5 | 7 | 88 | 87 | 86 | 3.8 | 11 | 7 |

The results were calculated from gas-liquid chromatographic analysis on a 1.5 meter length φ – ¼' column containing 20% Diethylene glycol adipate on Chromosorb W support; 30–60 mesh.

As can be seen from the data in Table 1, the production of the desired haloacetophenone is increased with increasing reaction time, while the co-production of the corresponding carbinol is reduced. Thus, irrespective of which metal phthalocyanine catalyst is used, the ratio of haloacetophenone to carbinol increases with increasing reaction time.

EXAMPLE 3

0.5 kg. of p-bromocumene dissolved in 1 kg. of o-dichlorobenzene were placed in a 2 liter, 316 stainless steel, magnetically stirred autoclave. After adding 0.5 gm. of copper phthalocyanine, the autoclave was closed and the reaction mixture heated to 140°C, while a current of air was passed in as described in Example 2. The temperature of the reaction mixture was mainever, even as regards the lowest such ratio, i.e., 1.6 to 1, which is lower than that of Example 1, the results must still be considered superior to those of Example 1 because the overall conversion of halocumene is higher than in Example 1.

In Examples 3–5, which describe the most preferred embodiment of the invention, the ratio of the yield of haloacetophenone to carbinol is at its greatest, i.e., 16 to 1 in Example 3.

Variations and modifications can, of course, be made without departing from the spirit and scope of the invention.

Having thus described our invention, what we desire to secure by Letters Patent and hereby claim is:

1. A process for the preparation of a haloacetophenone of the formula

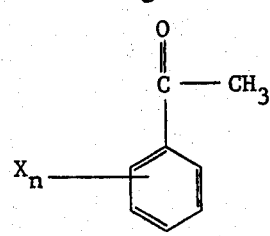

wherein X is chloro or bromo and n is 1–3, the halo substituents being meta and/or para to the

group, said process comprising oxidizing a halocumene of the formula:

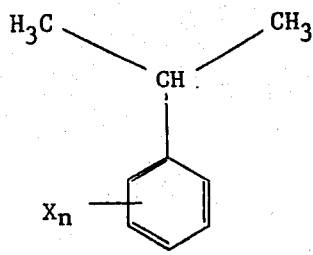

wherein X and n are as defined above at a temperature between 130°C. and 160°C. with air or oxygen, and in the presence of a catalytically effective amount of a metal phthalocyanine selected from the group consisting of iron, copper and cobalt phthalocyanine and in the presence of a dichlorobenzene as a solvent.

2. The process of claim 1, wherein said metal phthalocyanine is copper phthalocyanine.

3. The process of claim 1, wherein oxidation is effected at a pressure between 0.2 and 50 atm.

4. The process of claim 1, wherein n is 1 and the halo substituents are para to the keto group.

5. The process of claim 1, wherein the halocumene and the dichlorobenzene are present in a weight ratio of about 0.5 to 1.0.

6. The process of claim 1, wherein the dichlorobenzene is o-dichlorobenzene.

7. The process of claim 1, wherein the amount of catalyst is about 0.1% by weight based on the halocumene.

8. The process of claim 1, wherein the reaction is run for from about 2 to 4 hours.

* * * * *

UNITED STATES PATENT OFFICE
CERTIFICATE OF CORRECTION

Patent No. 3,954,876　　　　　　　　Dated May 4, 1976

Inventor(s) David VOFSI et al.

It is certified that error appears in the above-identified patent and that said Letters Patent are hereby corrected as shown below:

Title page, line 5 of the "Abstract"; "paraposition" should read -- para-position --.

Column 2, lines 59-60: "halocumenes" should read -- halocumene --.

Column 3, line 14: "1-chlorophenyl-isopropanol" should read -- 1-p-chlorophenyl-isopropanol --.

Signed and Sealed this

Twentieth Day of July 1976

[SEAL]

Attest:

RUTH C. MASON
*Attesting Officer*

C. MARSHALL DANN
*Commissioner of Patents and Trademarks*